United States Patent [19]

Geibel et al.

[11] Patent Number: 5,091,567
[45] Date of Patent: Feb. 25, 1992

[54] PROCESS FOR THE PREPARATION OF 1-AMINOMETHYL-1-CYCLOHEXANEACETIC ACID

[75] Inventors: Wolfram Geibel, Hünfeld; Johannes Hartenstein, Stegen-Wittental; Wolfgang Herrmann, Merzhausen; Joachim Witzke, Nimburg, all of Fed. Rep. of Germany

[73] Assignee: Gödecke Aktiengesellschaft, Berlin, Fed. Rep. of Germany

[21] Appl. No.: 570,487

[22] Filed: Aug. 21, 1990

[30] Foreign Application Priority Data

Aug. 25, 1989 [DE] Fed. Rep. of Germany ....... 3928182

[51] Int. Cl.$^5$ .............................................. C07C 61/08
[52] U.S. Cl. .................................... 562/507; 548/408; 548/554; 560/126; 562/504; 562/553; 564/448
[58] Field of Search ..................... 562/553, 504, 507; 548/554, 408; 560/126; 564/448

[56] References Cited

U.S. PATENT DOCUMENTS

| | | | |
|---|---|---|---|
| 2,812,334 | 11/1957 | Moffett et al. | 260/326.3 |
| 2,825,739 | 3/1958 | Allen | 562/553 |
| 3,253,039 | 5/1966 | Rylander | 562/553 |
| 3,417,090 | 12/1968 | Pelster | 562/553 |
| 3,594,419 | 7/1971 | Rosenthal | 564/448 |
| 3,595,875 | 7/1971 | Larkin | 548/554 |
| 3,624,127 | 11/1971 | Shaw et al. | 260/468 |
| 3,624,127 | 11/1971 | Shaw et al. | 260/468 |
| 3,766,271 | 10/1973 | Knifton | 564/448 |
| 4,024,175 | 5/1977 | Satzinger et al. | 260/514 |
| 4,087,544 | 5/1978 | Satzinger et al. | 424/305 |
| 4,894,476 | 1/1990 | Butler et al. | 562/504 |

FOREIGN PATENT DOCUMENTS

| | | | |
|---|---|---|---|
| 1094097 | 1/1981 | Canada . | |
| 7824 | 2/1980 | European Pat. Off. | 548/554 |
| 46-9810 | 3/1971 | Japan | 562/553 |
| 58-65255 | 4/1983 | Japan | 562/553 |
| 825562 | 12/1959 | United Kingdom . | |

OTHER PUBLICATIONS

*Journal of the American Chemical Society,* v. 83, No. 7, Apr. 19, 1961, pp. 1733-1738, W. S. Wadsworth et al., "The Utility of Phosphanate Carbanions in Olefin Synthesis".

*Organic Preparations and Procedures International,* v. 19, No. 6, 1987, pp. 471-475, Richard A. Bunce et al, "Michael Reaction of Nitromethane with Beta, Beta-Disubstituted Acrylate Esters".

Copending U.S. Application 399056, Filed 8-25-89.

*Primary Examiner*—Michael L. Shippen
*Attorney, Agent, or Firm*—Francis J. Tinney

[57] ABSTRACT

The instant invention concerns a novel process for the preparation of 1-aminomethyl-1-cyclohexaneacetic acid (gabapentin), a known compound useful for treating certain cerebral diseases such as epilepsy and dizziness.

14 Claims, No Drawings

PROCESS FOR THE PREPARATION OF 1-AMINOMETHYL-1-CYCLOHEXANEACETIC ACID

BACKGROUND OF THE INVENTION

Gabapentin is a generic term used to identify the chemical compound (1-aminomethyl)-1-cyclohexaneacetic acid

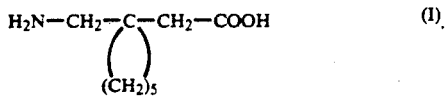

It is useful in therapy of certain cerebral disorders such as certain forms of epilepsy, faintness attacks, hypokinesia, and cranial traumas. U.S. Pat. Nos. 4,024,175 and 4,087,544 cover the compound and its uses. They also disclose an acid salt, i.e., gabapentin hydrochloride hydrate in a ratio of 4:4:1 and a sodium salt of gabapentin hydrate in a ratio of 2:1. U.S. Pat. No. 4,894,476 describes gabapentin monohydrate and a process for producing it. These patents are incorporated by reference.

The patents describe various processes for the preparation of this and similar compounds of general formula

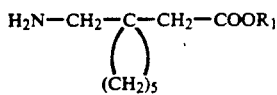

wherein $R_1$ is a hydrogen atom or a lower alkyl radical and n is 4, 5, or 6 and the pharmaceutically acceptable salts thereof, which depend upon known methods used for the preparation of primary amines or amino acids.

Examples of the syntheses end in an isocyanate or urethane that can be converted into the desired (1-aminomethyl)-1-cyclohexaneacetic acid by acidic hydrolysis to give an acid or basic hydrolysis to give a basic salt or followed by acidification to give an acid salt.

DETAILED DESCRIPTION OF THE INVENTION

The present invention is concerned with a process for the preparation of gabapentin (1-aminomethyl-1-cyclohexaneacetic acid).

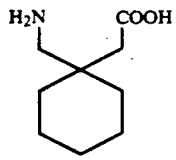

Gabapentin is a medicament described in Germany Patents 24 60 891 and 25 43 821 for the therapy of certain cerebral diseases, for example epilepsy and cases of dizziness.

Various processes are known for the preparation of gabapentin and related compounds. For example, gabapentin can be prepared by converting 1,1-cyclohexanediacetic acid, via a reactive acid derivative, into the azide which is subsequently subjected by thermal decomposition to a Curtius reaction.

For reasons of safety, the process is not very suitable for technical use since the azide formed can easily explode in the case of heating or working up (stirring with acid).

Gabapentin can also be obtained by the Lossen rearrangement of the corresponding hydroxamic acid. The process previously known for the preparation of gabapentin via the Lossen rearrangement takes place via the following eight reaction steps:

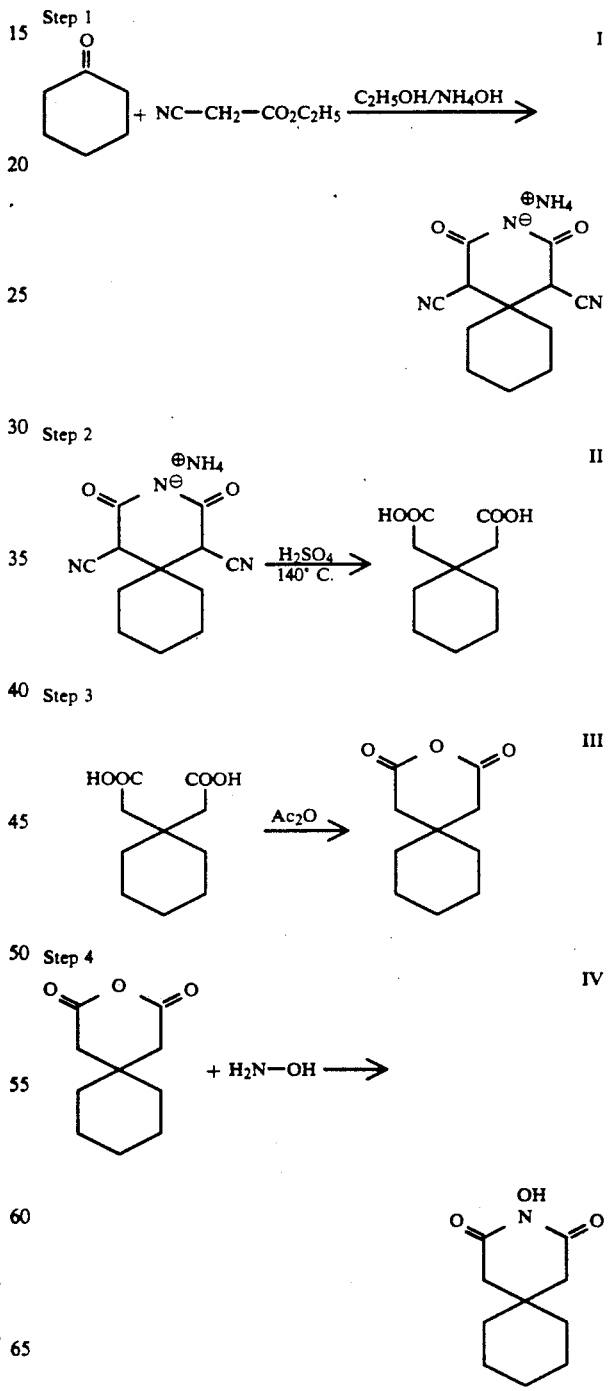

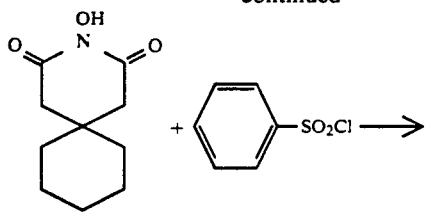

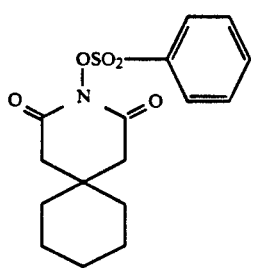

Step 6

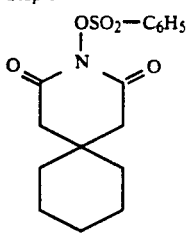

Et₃N/MeOH →

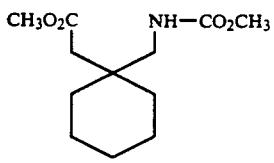

Step 7

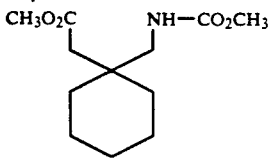

HCl/H₂O →

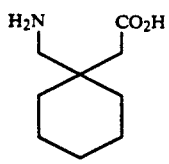

Step 8

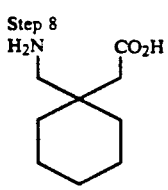

.HCl.½H₂O Ionenaustauscher →

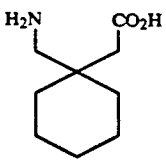

The above process has some serious disadvantages which are briefly as follows:

the total yield over all of the steps is only 30%;
because of the many reaction steps, the process requires a relatively large expenditure of time and labor and therefore a high production cost;
in reaction Step 1, work is carried out with large amounts of gaseous ammonia at low temperatures;
in reaction Step 2, 80% sulphuric acid is used as solvent at 160° C.; the removal of this and of further acids used in the process of production results in toxic waste water;
the process requires, in part, expensive adjuvant reagents which are not incorporated into the end product and thus contribute substantially to the high costs of production.

The instant invention provides a new process for the preparation of gabapentin which:

(1) involves fewer reaction steps and thus requires shorter time and less labor;
(2) the total yield is greater than that of the known process;
(3) the costs of production are lower;
(4) the process should be useful on an industrial scale;
(5) the process should ensure a minimum danger to people and have a small impact on the environment.

The present invention, provides a process for the preparation of gabapentin according to the principle of a Michael condensation, which is characterized by the following reaction steps:

(a) reaction of cyclohexanone with a phosphonic acid ester compound to give a cyclohexylideneacetic acid ester;

(b) reaction of the cyclohexylideneacetic acid ester with nitromethane to give the corresponding 1-nitromethylcyclohexaneacetic acid ester;

(c) reduction of the 1-nitromethylcyclohexaneacetic acid ester to the corresponding 1-aminomethylcyclohexene-acetic acid ester and 2-aza-spiro[4,5]decan-3-one;

(d) conversion of the products obtained in Step c into 1-aminomethyl-1-cyclohexaneacetic acid salt by means of dilute acid;

(e) liberation of the 1-aminomethyl-1-cyclohexaneacetic acid from the salt by means of ion exchangers, wherein in Step (a) the cyclohexanone is first reacted at ambient temperature with potassium hydroxide before the phosphonic acid ester is added thereto; in Step (b) dimethyl sulphoxide is used as solvent and an alkali metal carbonate as catalyst; and in Step (c) work is carried out at an elevated temperature above 100° C.

The cyclohexylideneacetic acid ester is a lower alkyl ester with alkyl from 1 to 6 carbon atoms, preferred is the ethyl ester.

The process of the present invention is a simple, quick and cost-effective preparation of gabapentin. The process consists of five reaction steps and gives a total yield of about 50%, in comparison with 30% in the case of the known process. By recycling of unreacted starting material in reaction Step (d) to the reaction process, the yield can be further increased by up to 15%.

The process according to the present invention is superior to the known process due to the short and simple procedures involved. All reactions are complete after a maximum of 4 hours. The reaction in Step 1 takes place at ambient temperature. All the reaction products are extracted from the reaction mixture or are obtained directly by removal of the solvent. The material isolated in Step (d) is pure according to HPLC and the purity of the products of the other steps is greater than 95% so that no purification operations are necessary.

The new, optimized process according to the present invention is illustrated by the following Scheme I.

Step (a)

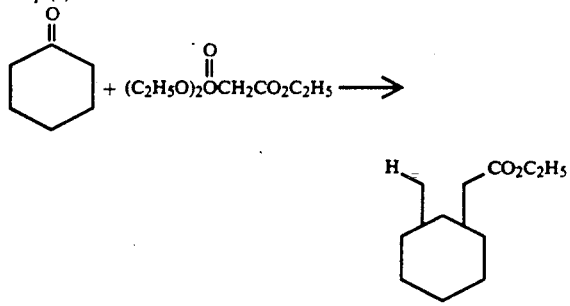

step b.)

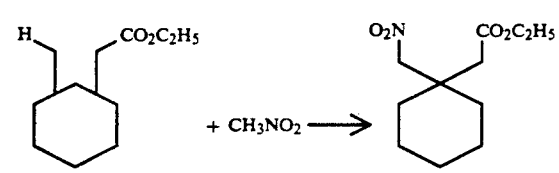

Step c.)

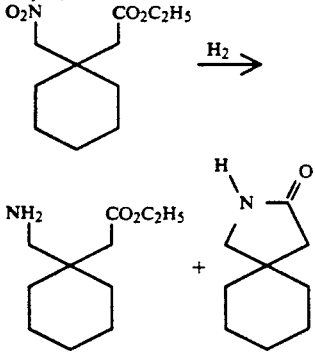

step d.)

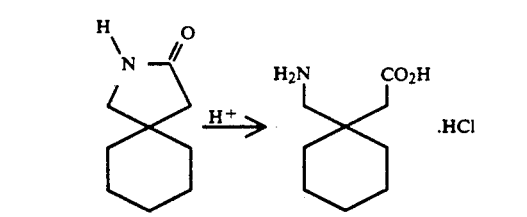

step e.)

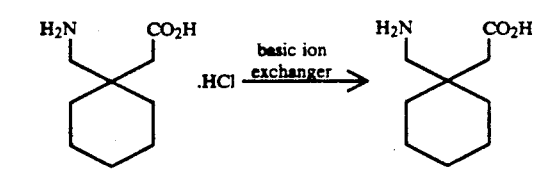

In reaction Step (a) of the process according to the present invention, cyclohexanone is reacted to give cyclohexylideneacetic acid ester. For this purpose, the phospho-organic compound is first reacted with a base, for example, sodium hydride, and subsequently with cyclohexanone. Instead of sodium hydride, sodium hydroxide or potassium hydroxide can be used and thus more safely handled. Loss of yield and by-products (ester cleavage and decomposition) then take place.

Surprisingly, it has been found that by an altered course of the reaction, even with the use of potassium hydroxide, the yield of product and the purity can be greatly increased and the formation of by-products can be avoided. In this way, it becomes possible to avoid more laborious purification operations (vacuum distillation). In the case of this altered course of the reaction, cyclohexanone is first reacted at ambient temperature with potassium hydroxide before the phosphonic acid ester is added. After a short post-reaction at ambient temperature, the reaction is quenched by the addition of water and the product is extracted from the aqueous solution with petroleum ether. After removal of the solvent, the product is obtained in a yield of more than 90% and with a purity of 98%.

In reaction Step 2 of the process of the present invention, a Michael condensation of nitromethane to the product of Step 1 with base catalysis takes place. The addition of nitromethane to $\beta,\beta$-disubstituted aorylic acid esters like the product of Step 1 (cyclohexylideneacetic acid ester) is made difficult by the insufficient activation by one ester group and by the steric hindrance of the substituents. It is known in the art that, in the case of less activated reaction components, nitromethane in large excess with or without solvent, usually under reflux can be used.

In *J. Org. Chem.*, 50, 2806/1985 the Michael condensation of acrylic acid esters without using an excess of nitromethane is described. However, first the stoichiometric formation of the salt of nitromethane with bases, such as potassium hydroxide or potassium tert.-butylate, is necessary. Furthermore, in the case of the described $\beta,\beta$-disubstituted compounds, the double bond is to be activated by a further electron-attracting group.

The Michael condensation requires the presence of basic catalysts, for example potassium hydroxide, various amines, alcoholates, metal fluorides or the like. Tetraalkylammonium fluorides are also very effective catalysts for the Michael condensation. Under such conditions, i.e., with a large excess of nitromethane, the described reaction with the product of Step 1 can be carried out on a laboratory scale, in which case tetraethylammonium fluoride or potassium hydroxide are the catalysts of choice. However, these conditions could not be used for the process according to the present invention since, as is known, nitromethane forms compounds capable of explosion with strong bases and is capable of explosion with the help of primers.

Nitromethane exists in a tautomeric equilibrium with the corresponding nitronic acid. With potassium hydroxide, nitronic acid forms an extremely unstable salt which is highly sensitive to impact. Amines in turn also give a detonation-sensitiva mixture. In general, alkaline solutions of nitromethane are known not to be stable when they are heated or stored for a comparatively long time.

Another reason for the non-usability of the above conditions for the process according to the present invention is, on the one hand, the cleavage of the products of Step 1 by strong bases to give a carboxylic acid and, on the other hand, the fact that, in this special case, strong bases, such as potassium hydroxide and tetraalkylammonium fluorides, catalyze the rearrangement of the double bond in the ring. The formation of the compounds with a rearranged double bond in the ring is almost quantitative. It is thermodynamically preferred in comparison with the product of Step 1 with conjugation of the double bond and ester function. In the case of the absence of nitromethane, the product of Step 1 reacts, with base catalysis, in less than 15 minutes to the more stable by-product 1-cyclohexeneacetic acid ester. In the presence of equimolar amounts of nitromethane, the by-product formation in comparison with the formation of the product of Step 2 is still preferred and, after working up, about 10% of the desired product of Step 2 is obtained and about 90% 1-cyclohexeneacetic acid ester.

Because of the potential danger of nitromethane, on the one hand, and the undesirable side reactions, on the other hand, an attempt must be made, a) to avoid the use of strong bases and, b) to reduce the proportion of nitromethane if possible to the proportion necessary for the reaction, i.e., to the equivalent amount.

Accordingly, it was quite unexpected to have the reaction take place with such good yields when the proportion of nitromethane is reduced to the necessary minimum amount, weak bases are used as catalysts and an additional solvent is used.

Surprisingly, it has been found that in reaction Step 2, in spite of the limited conditions, yields of 90% and purities of $\geq 90\%$ can be achieved and no by-products are formed when dimethyl sulphoxide is used as solvent in conjunction with catalytic amounts (10–50 mole%) of potassium carbonate or sodium carbonate as basic catalyst. In detail, the procedure is such that nitromethane is added slowly and continuously in equimolar amount (with 10% to 50% 10 excess), together with the product of Step 1, to a reaction mixture of solvent and catalyst at 95° to 100° C. However, nitromethane can also be added continuously alone to a reaction mixture of solvent, catalyst and the product of Step 1 at 95° to 100° C. However, by-products are formed. In any case, by the continuous addition of nitromethane, it is ensured that nitromethane always reacts away and can at no time exist in comparatively large amounts from which a potential danger could result.

The third reaction step of the process according to the present invention is the catalytic reduction of the nitro group to the amino group. For this purpose, the product of reaction Step 2 is reacted with hydrogen in the presence of a noble metal catalyst, for example palladium on active carbon. As solvent, acetic acid, ethanol or also ethanol with aqueous hydrochloric acid can be used. From this reaction there normally results two products, the cyclized product (lactam) and ethyl 1-aminomethyl-1-cyclohexaneacetate. We have found that, at a sufficiently high temperature, preferably at 100° to 125° C., the "lactam" is obtained exclusively in a yield of more than 90%. After removal of the catalyst and of the solvent, the lactam is, without further purification, hydrolyzed in reaction Step 4 of the process according to the present invention with aqueous hydrochloric acid at boiling temperature to give gabapentin hydrochloride. Depending upon the acid concentration, there is a conversion into up to 80% gabapentin hydrochloride. The unreacted lactam is recovered by extraction and again subjected to the hydrolysis. From the remaining aqueous solution, gabapentin hydrochloride is obtained in 60% to 70% yield with a purity of 99%.

The purity achieved makes further purification superfluous so that, in reaction Step 5 of the process according to the present invention, the free amino acid gabapentin can be obtained directly from the hydrochloride. For this purpose, a 20% aqueous solution of gabapentin hydrochloride is passed over a column filled with a weakly basic anion exchanger. From the resulting aqueous solution, by gentle evaporation in a vacuum and subsequent crystallization from methanol, gabapentin can be obtained with high purity in a yield of 80% to 90%.

In an especially preferred Step 1, the cyclohexanone and the phosphonic acid ester are taken and potassium hydroxide is introduced, while stirring, into this homogeneous phase. In a rapid and exothermal reaction, which is kept at 30° to 40° C. by cooling and a measured rate of introduction of the potassium hydroxide, the reaction is practically complete.

Furthermore, we have ascertained that the catalytic hydrogenation in ethanol as solvent already leads quickly and practically to the lactam even at temperatures above 60° C.

The following Examples are given for the purpose of illustrating the present invention but are not intended to limit the scope in any way.

EXAMPLE 1

Preparation of ethyl cyclohexylideneacetate (Step 1)

70.2 g (1.10 mole) Potassium hydroxide powder (content 88%) are suspended in 168 mL tetrahydrofuran and mixed dropwise, while cooling to 20° to 25° C., with 98.2 g (1.0 mole) cyclohexanone. Stirring is continued for 15 minutes and subsequently 246.6 g (1.10 mole) triethyl phosphonoacetic acid are added dropwise thereto at ambient temperature in the course of 15 to 30 minutes, followed by stirring for 1 hour at ambient temperature.

The reaction mixture is subsequently mixed with water and the organic phase is separated off. The aqueous phase is again shaken out with methylene chloride. The combined organic phases are washed with water, dried over anhydrous sodium sulphate and then the solvent is distilled off in a vacuum. 158.7 g Ethyl cyclohexylideneacetate in the form of an oil are obtained; yield 94.3% of theory. Content according to HPLC. and GC: 98% to 99%.

EXAMPLE 2

Preparation of ethyl 1-nitromethyl-1-cyclohexaneacetate (Step 2)

To a mixture of 64.72 g (0.469 mole) potassium carbonate suspended in 469.5 mL dimethyl sulphoxide is measured in, during the course of 1 to 2 hours at 95° C., a solution of 158 g, (0.939 mole) ethyl cyclohexylideneacetate and 85.94 g (1.408 mole) nitromethane. After completion of the addition, stirring is continued at 95° C. for 2 to 3 hours. Subsequently, with ice-water cooling, the reaction solution is acidified with about 150 mL concentrated hydrochloric acid and diluted with 1.5 L of water. The resultant phases are separated and the aqueous phase is extracted several times with petroleum ether. The combined organic phases are washed neutral with water and dried over anhydrous sodium sulphate. The solvent is subsequently distilled off in a vacuum. 190.3 g Ethyl 1-nitromethyl-cyclohexaneacetate in the form of an oil are obtained; yield 88.4% of theory. Composition according to HPLC: 90% of the desired product of Step 2 and 6% ethyl cyclohexylideneacetate (Step 1).

EXAMPLE 3

16.8 g (0.1 mole) Ethyl cyclohexylideneacetate and 13.8 g (0.1 mole) potassium carbonate are heated to 95° to 100° C. in 50 mL, dimethyl sulphoxide and mixed with a solution of 9.2 g (0.15 mole) nitromethane in 10 mL dimethyl sulphoxide over the course of 1 hour. After a postreaction for 1 hour, the reaction mixture is worked up as in Example 2. 19.26 g Product containing 61.4% ethyl 1-nitromethylcyclohexaneacetate, 27.5% of starting compound and 7.8% of by-product (ethyl 1-cyclohexeneacetate).

EXAMPLE 4

16.8 g (0.1 mole) Ethyl cyclohexylideneacetate, 9.2 g, (0.15 mole) nitromethane and 0.64 g (0.01 mole) potassium hydroxide (content 88%) in 40 mL dimethyl sulphoxide are stirred for 2 hours at 100° C. The reaction mixture is worked up analogously to Example 2 to give 20.5 g ethyl 1-nitromethyl-1-cyclohexaneacetate (89.4% of theory). According to GC., the content is 82.8% and 10.2% of starting compound and 4.1% of by-product are obtained (see Example 3).

EXAMPLE 5

16.8 g (0.1 mole) Ethyl cyclohexylideneacetate and 0.64 g (0.01 mole) potassium hydroxide (content 8%) in 40 mL dimethyl sulphoxide are heated to 100° C and mixed dropwise for 1 hour with 9.2 g (0.15 mole) nitromethane in 10 mL dimethyl sulphoxide. The 0 reaction is allowed to continue for 2 hours and then worked up analogously to Example 2. 17.6 g of residue containing 26% ethyl 1-nitromethyl-1-cyclohexaneacetate, 30.2% of starting compound and 35.9% of by-product are obtained (see Example 3).

EXAMPLE 6

16.8 g (0.1 mole) Ethyl cyclohexylideneacetate and 2 g (0.01 mole) tetraethylammonium fluoride dihydrate were heated to 100° C. in 40 mL dimethyl sulphoxide and mixed continuously for 1 hour with 9.2 g (0.15 mole) nitromethane. The reaction is allowed to continue for 2 hours at 100° C. and then worked up analogously to Example 2. 15.4 g of an oily residue containing about 10% of the desired Step 2 product and about 90% ethyl 1-cyclohexeneacetate are obtained (see Example 3).

EXAMPLE 7

16.8 g (0.1 mole) Ethyl cyclohexylideneacetate and 4 g (0.02 mole) tetraethylammonium fluoride dihydrate in 50 mL nitromethane are heated under reflux for 3 hours. Subsequently, the reaction mixture is mixed with 100 mL dilute hydrochloric acid and extracted several times with dichloromethane. The organic phases are washed neutral and dried. After removal of the solvent in a vacuum, an oily residue, 20.9 g (91.3% of theory) of the Step 2 product with a content of 84% (GC) is obtained.

EXAMPLE 8

Preparation of 2-aza-spiro[4,5]decan-3-one (Step 3)

190 g (0 82 mole) Ethyl 1-nitromethyl-1-cyclohexaneacetate in 3168 mL ethanol are hydrogenated for 4 hours at 125° C. in the presence of 62.9 g 10% palladium-carbon. At the end of the take up of hydrogen, the catalyst is filtered off and the colorless solution obtained is distilled to dryness in a vacuum. 116.2 g 2-Azaspiro[4,5]decan-3-one in the form of a colorless crystallizate are obtained; yield 91.6% of theory. Content 97.1% (GC); m.p. 88° to 90° C.

EXAMPLE 9

Preparation of 1-aminomethyl-1-cyclohexaneacetic acid hydrochloride (Step 4)

89 g (0.581 mole) 2-Aza-spiro[4,5]decan-3-one are stirred under reflux for 4 hours with semiconcentrated hydrochloric acid. The reaction mixture is cooled to ambient temperature, diluted with water and extracted with methylene chloride for the removal of the starting material. The aqueous phase is evaporated to dryness in a vacuum and the residue obtained is mixed with acetone. Upon standing, 79.85 g, 1-aminomethyl-1-cyclohexaneacetic acid hydrochloride (64.7% of theory) crystallize out; content 99%; m.p. 123° to 127° C.

From the mother liquor, by evaporation, a further 6.2 g of product can be isolated (5% of theory). From the methylene chloride phase, by removal of the solvent there is recovered unreacted 2-aza-spiro[4,5]-decan-3-one (20 to 25 g) which is again reacted with semiconcentrated hydrochloric acid.

EXAMPLE 10

Preparation of 1-aminomethyl-1-cyclohexaneacetic acid (Step 5)

2 kg (9.42 mole) 1-Aminomethyl-1-cyclohexaneacetic acid hydrochloride are dissolved in water and eluted over a column filled with ion exchanger. The aqueous solution obtained of the free amino acid is gently evaporated to dryness in a vacuum and the residue is crystallized from methanol. 1.339 kg 1-Aminomethyl-1-cyclohexaneacetic acid are obtained (83% of theory); m.p. 165° to 167° C.; purity >99.5%.

EXAMPLE 11

Preparation of ethyl cyclohexylideneacetate (Step 1)

3.66 kg (37.29 mole) Cyclohexanone are mixed with 8.87 kg (39.56 mole) triethyl phosphonoacetate. While cooling, the mixture is mixed portionwise with 2.51 kg (38.02 mole) potassium hydroxide powder (content 85%) maintaining a temperature of 30° to 40° C. After 1 hour, the reaction mixture is mixed with 18 L of water and subsequently repeatedly extracted with n-hexane. The combined organic phases are washed with water, dried over anhydrous sodium sulphate and the solvent then distilled off in a vacuum. 5.78 kg Ethyl cyclohexylideneacetate in the form of an oil are obtained (92.1% of theory). Content according to HPLC and GC. 96.5% to 99.5%.

EXAMPLE 12

A mixture of 5.00 kg (50.94 mole) cyclohexanone and 12.00 kg (53.53 mole) triethyl phosphonoacetate is mixed portionwise with 3.36 kg (52.70 mole) potassium hydroxide powder, maintaining a temperature of 30° to 40° C. Then the reaction mixture is further stirred for 1 hour. The reaction mixture is then divided into two portions, each of 10.15 kg.

(a) 10.15 kg, were worked up analogously to the description of Example 1. 3.92 kg Ethyl cyclohexylideneacetate in the form of an oil are obtained; 91.5% of theory. Content according to HPLC 99.8%.

(b) 10.15 kg of the reaction mixture are mixed with 9.8 L dimethyl sulphoxide. 16.06 kg of this mixture contain about 18 mole of the product of Step 1 and are used for the reaction in Step 2 (Example 3).

EXAMPLE 13

Preparation of ethyl 1-nitromethyl-1-cyclohexaneacetate (Step 2)

1.294 kg (9.36 mole) Potassium carbonate are suspended in 8 L dimethyl sulphoxide and heated to 110° to 115° C. 16.06 kg of dimethyl sulphoxide solution of Step 1 (as described in Example 12b); corresponding to 18 mole of product of Step 1 are mixed with 1.72 kg (28.18 mole) nitromethane and in the course of 3.5 hours, added dropwise at 110° to 115° C. into the potassium carbonate-dimethyl sulphoxide suspension. The reaction mixture is further stirred for 4 hours at 110° C. and left to cool overnight to ambient temperature. 2.50 kg of the reaction solution are removed for analytical purposes. The rest of the mixture is mixed with 40 L of water and subsequently extracted several times with n-hexane. The combined organic phases are washed with water, dried over anhydrous sodium sulphate and the solvent then distilled off in a vacuum. 3.38 kg Ethyl 1-nitromethyl-1-cyclohexaneacetate in the form of an oil are obtained; 83% of theory. Content according to HPLC: 86.5% of the product of Step 2 and 4.5% of the product of Step 1.

EXAMPLE 14

98.15 g (1.00 mole) Cyclohexanone are mixed with 35.4 g (1.05 mole) ethyl phosphonate and mixed at 25° to 30° C. with 66.1 g (1.04 mole) potassium hydroxide powder (content 88%). The reaction mixture is further stirred for 30 minutes and successively mixed with 150 mL dimethyl sulphoxide and 86.0 g (1.41 mole) nitromethane. This solution is added dropwise at 110° to 115° C. over 35 minutes to a suspension of 64.7 g (0.47 mole) potassium carbonate in 470 mL dimethyl sulphoxide. Then stirring is continued for 2 to 3 hours and the reaction mixture is mixed with water and subsequently extracted several times with n-hexane. The combined organic phases are washed with water, dried over anhydrous sodium sulphate and the solvent then distilled off in a vacuum. 191.5 g ethyl 1-nitromethyl-1-cyclohexaneacetate in the form of an oil are obtained (yield 83% of theory). Composition according to HPLC: 88.7% of the product of Step 2 and 6.3% of the product of Step 1.

EXAMPLE 15

Preparation of 2-aza-spiro[4,5]decan-3-one (Step 3)

30 g (0.13 mole) Ethyl 1-nitromethyl-1-cyclohexaneacetate (content according to GC. 83%) in 300 mL ethanol are hydrogenated in the presence of palladium-carbon (10%) at 60° to 80° C. and 0.6 bar for 3 hours. Upon completion, the catalyst is filtered off and the almost colorless solution is distilled off to dryness in a vacuum. A pale brown crystallizate is obtained, 19.0 g 2-aza-spiro[4,5]decan-3-one (95% of theory). Content according to GC: 83%.

We claim:

1. A process for the preparation of

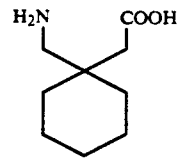

which comprises:
   (a) reacting cyclohexanone with a phosphonoacetic acid ester and a base to produce the corresponding cyclohexylideneacetic acid ester,
   (b) reacting the cyclohexylideneacetic acid ester from Step (a) with nitromethane in the presence of a basic catalyst to produce the corresponding 1-nitromethyl-1-cyclohexaneacetic acid ester,
   (c) reducing the 1-nitromethyl-1-cyclohexaneacetic acid ester from Step (b) with hydrogen in the presence of a noble metal catalyst to the corresponding 1-aminomethyl-1-cyclohexaneacetic acid ester and 2-aza-spiro[4,5]-decan-3-one,
   (d) converting the products of Step (c), 1-aminomethyl-1-cyclohexaneacetic acid ester and 2-aza-spiro[4,5]-decan-3-one, into 1-aminomethyl-1-cyclohexaneacetic acid salt using a dilute acid, and
   (e) converting the salt from Step (d) to the 1-aminomethyl-1-cyclohexaneacetic acid.

2. A process according to claim 1 wherein in Step (a) cyclohexanone is reacted with a base at about ambient temperature before reacting it with a phosphonoacetic acid ester.

3. A process according to claim 2 wherein the base is selected from sodium hydride, sodium hydroxide, and potassium hydroxide.

4. A process according to claim 1 wherein in Step (b) dimethyl sulphoxide is used as a solvent and an alkali metal carbonate is used as a catalyst.

5. A process according to claim 1 wherein in Step (c) the reduction is carried out at a temperature of from about 100° C. to about 125° C., with a noble metal catalyst.

6. A process according to claim 3 wherein the base is potassium hydrodroxide.

7. A process according to claim 4 wherein in Step (b) the alkali metal carbonate is selected from the group consisting of potassium carbonate and sodium carbonate.

8. A process according to claim 7 wherein the alkali metal carbonate is potassium carbonate.

9. A process according to claim 5 wherein in Step (c) the reduction is carried out at a temperature of about 125° C.

10. A process according to claim 1 wherein the Step (b) the cyclohexylideneacetic acid ester is ethyl cyclohexylideneacetate.

11. A process according to claim 1 wherein in step (c) the noble metal catalyst is palladium on active carbon.

12. A process according to claim 1 wherein in step (d) the dilute acid is hydrochloric acid.

13. A process according to claim 1 wherein in step (e) an aqueous solution of 1-aminomethyl-1-cyclohexaneacetic acid hydrochloride is passed over a column filled with a weakly basic anion exchanger to afford 1-aminomethyl-1-cyclohexaneacetic acid.

14. A process according to claim 1 wherein in 1-aminomethyl-1-cyclohexaneacetic acid is converted to a pharmaceutically acceptable acid salt thereof.

* * * * *

UNITED STATES PATENT AND TRADEMARK OFFICE
CERTIFICATE OF CORRECTION

PATENT NO. : 5,091,567
DATED : February 25, 1992
INVENTOR(S) : Geibel, et al

It is certified that error appears in the above-indentified patent and that said Letters Patent is hereby corrected as shown below:

Column 12, line 44, delete "hydrodroxide" and insert --hydroxide--.

Signed and Sealed this

Eighth Day of June, 1993

Attest:

MICHAEL K. KIRK

Attesting Officer

Acting Commissioner of Patents and Trademarks